(12) United States Patent
Wu

(10) Patent No.: US 8,372,450 B2
(45) Date of Patent: Feb. 12, 2013

(54) CHINESE HERBAL COMPOSITION FOR THE TREATMENT OF MACULAR DEGENERATION AND THE PROCESS FOR MANUFACTURING THE SAME

(76) Inventor: Jerry Yourui Wu, Mountain View, CA (US)

(*) Notice: Subject to any disclaimer, the term of this patent is extended or adjusted under 35 U.S.C. 154(b) by 0 days.

(21) Appl. No.: 13/463,795

(22) Filed: May 3, 2012

(65) Prior Publication Data

US 2012/0282330 A1    Nov. 8, 2012

(30) Foreign Application Priority Data

May 6, 2011  (CN) .......................... 2011 1 0117394

(51) Int. Cl.
| | | |
|---|---|---|
| A61K 36/00 | (2006.01) | |
| A61K 36/537 | (2006.01) | |
| A61K 36/815 | (2006.01) | |
| A61K 36/79 | (2006.01) | |
| A61K 36/539 | (2006.01) | |
| A61K 36/232 | (2006.01) | |
| A61K 36/804 | (2006.01) | |
| A61K 36/481 | (2006.01) | |
| A61K 36/8984 | (2006.01) | |
| A61K 36/482 | (2006.01) | |
| A61K 36/68 | (2006.01) | |
| A61K 36/884 | (2006.01) | |
| A61K 36/488 | (2006.01) | |
| A61K 36/076 | (2006.01) | |

(52) U.S. Cl. ........................................ 424/725; 424/746
(58) Field of Classification Search ........................ None
See application file for complete search history.

(56) References Cited

U.S. PATENT DOCUMENTS

| | | | |
|---|---|---|---|
| 6,264,995 B1 | 7/2001 | Newmark et al. | |
| 6,537,581 B2 | 3/2003 | Tao | |
| 7,205,004 B2 | 4/2007 | Xia | |
| 2002/0031559 A1 | 3/2002 | Liang et al. | |
| 2004/0058015 A1 | 3/2004 | Tao | |
| 2005/0058730 A1 | 3/2005 | Wan et al. | |
| 2006/0020046 A1 | 1/2006 | Goralczyk et al. | |
| 2009/0220667 A1 | 9/2009 | Johnson | |
| 2010/0068306 A1 | 3/2010 | Chou | |

FOREIGN PATENT DOCUMENTS

| | | |
|---|---|---|
| CN | 101474368 A | 7/2009 |
| CN | 101595981 A * | 12/2009 |

OTHER PUBLICATIONS

Waisbourd, M., Loewenstein A., et al. Targeting vascular endothelial growth factor: a promising strategy for treating age-related macular degeneration. Drugs Aging.2007; 24(8):643-62.
Schmidt-Erfurth, U, Pollreisz A., et al. Antivascular endothelial growth factors in age-related macular degeneration. Dev Ophthalmol. 2010; 46:21-38. EpubAug. 10, 2010.
Klein R et al. Prevalence of age-related macular degeneration in the US population. Arch Ophthalmol. Jan. 2011; 129 (1): 75-80.
Congdon, N, et al. Causes and prevalence of visual impairment among adults in the United States. Arch Ophthalmol. Apr. 2004; 122(4): 477-85).
Xu, L., et al. Associated factors for age-related maculopathy in the adult population in China: the Beijing eye study. Br.J Ophthalmol. Sep. 2006. 90(9): 1087-1090.
Wu, L., et al. Causes and 3-year-incidence in Jing-An District, Shanghai, China 2001-2009. BMC Ophthalmol. 2011;11:10.
Cheung, C.M., et al. Prevalence of and risk factors for age-related macular degeneration in a multiethnic Asian cohort. Arch Ophthalmol. Dec. 12, 2011 (Epub ahead of print).
Hageman, G.S. Age-related macular degeneration. Mar. 30, 2011. webvision.med.utah.edu/book/part XII/cell biology of macular degeneration/amd.
Chakravarthy, U., et al. Clinical risk factors for age-related macular degeneration: a systematic review and meta-analysis. BMC Ophthalmol. 2010; 10: 31.
Penn, J.S. et al. Vascular endothelial growth factor in eye disease. Prog Retin EProg Retin Eye Res. 2008;27: 331-371.
Wiktorowska-Owcarek A, Nowark JZ. Pathogenesis and prophylaxis if A MD:focus on oxidative stress and antioxidans. Postepy Hig Med Dosw. 2910 Jul. 28; 64:333-43, 2010.
Holz, F.G., et al. Age-related macular degeneration. p. 14, Springer 2004.
Wu, XW, et al. Pathogenesis and treatment of age-related macular degeneration. Aug. 6, 2009. www.wuxingwei.haodf.com.
Taylor F., Drugs affecting the Eye. Aust. Fam Physician. Aug. 1985:14 (8): 744-5.
Wang, N.L., Wei, WB, et al. Beijing Tongren Hospital Ophthalmic Seminars. p. 359, Zhengzhou University Press, Zhengzhou, 2005.
Beatty, S., Koh, H., et al. The role of oxidative stress in the pathogenesis of age-related macular degeneration. Surv Ophthalmol. Sep.-Oct. 2000; 45(2):115-34.
Gragoudas, E.S., et al. Pegaptanib for neovascular age-related macular degeneration. N Engl J Med. Dec. 30, 2004; 351(27): 2805-16.

(Continued)

*Primary Examiner* — Quiwen Mi
(74) *Attorney, Agent, or Firm* — Intellectual Property Law Group LLP

(57) ABSTRACT

The present invention provides a Chinese herb composition for the treatment of macular degeneration and its preparation method. The composition comprises *Salviae miltiorrhizae, Chuanxiong rhizoma, Lycii fructus, Chrysanthemi flos, Schisandrae chinensis fructus, Imperatae rhizoma*, and *Scutellariae radix*, where the number of units by weight are: 0.8-3.0 units of *Salviae miltiorrhizae*, 0.3-2.0 units of *Chuanxiong rhizoma*, 0.6-2.4 units of *Lycii fructus*, 0.5-2.0 units of *Chrysanthemi flos*, 0.2-1.2 units of *Schisandrae chinensis fructus*, 0.9-6.0 units of *Imperatae rhizoma*, and 0.5-2.0 units of *Scutellariae radix*. The preparation method includes taking concentrated powder of each ingredient according to the number of units prescribed and mixing them together. The Chinese herb composition, conveniently delivered orally or parenterally, has been clinically proven to be safe and effective for all types of macular degeneration regardless of wet or dry forms.

17 Claims, No Drawings

OTHER PUBLICATIONS

Sunness, J.S. The natural history of geographic atrophy, the advanced atrophic form of age-related macular degeneration. Mol Vis. 1999;5:25.

Dunaief, J.L., et al. The Role of Apoptosis in Age-Related Macular Degeneration, Arch Ophthalmol. 2002;120:1435-1442.

Lim, J.I. Age-related macular degeneration. Second edition, Part I pp. 1-5. Informa, New York, 2008.

Zarbin, Marco A. Current concepts in the pathogenesis of age-related macular degeneration. Arc Ophthalmol.2004;122:598-614.

Ursekar, T.N. Classification, Etiology and Pathology of Myopia. Indian J Ophthalmol. 1983; 31:709-11.

Grossniklaus, H.E., Green, W.R. Pathologic findings in pathologic myopia. Retina (Philadelphia, Pa.) 1992, 12(2):127-33.

Klein RM, Green S. The development of lacquer cracks in pathologic myopia. Am J Ophthalmol. Sep. 15, 1988;106(3):282-5.

Ohno-Matsui, K. et al. The Progression of Lacquer Cracks in Pathologic Myopia. Retina. 1996;16(1):29-37.

Saw SM et al. Myopia and associated pathological complications. Ophthalmic and Physiological Optics. Sep. 2005; 25( 5): 381-391.

Zachariah G, Idiculla T, et al. Macular dystrophystrophy in a young male with corneal dystrophy among sisters. Oman J Ophthalmol. May-Aug. 2011; 4(2):95-96.

Brown, D.M. et al. ANCHOR Study Group, Ranibizumab versus vertiporfin for neovascular age-related macular degeneration. N Eng J Med.Oct. 2006;355(14):1432-44).

Rosenfeld PJ, Rich RM, Ranibizumab: Phase III clinical trial results. Ophthalmol Clin North Am. Sep. 19, 2006 (3): 361-72.

Rosenfeld PJ, Brown DM. Heier JS, et al. Ranibizumab for neovascular age-related macular degeneration. N. Eng J Med. 2006;355(14):1419-1431.

Abouammoh M, Sharma S. Ranibizumab versus Bevaczumab for the treatment of neovascular age-related macular degeneration. Curr Opin Ophthalmol. May 2011; 22(3):152-8.

The CATT research group, Ranibizumab and Bevaczumab for neovascular age-related macular degeneration. N Eng J Med May 19, 2011;364(20)1897-1908.

John Geyer, www.medpagetoday.com Nov. 19, 2011.

Bhisitjul RB, Vascular endothelial growth factor biology: clinical applications for ocular treatments. B. J Ophthalmol.2006; 90: 1542-1547.

Scheler RH. Napoleone Ferrara Named 2010 Lasker Award Winner http://www.gene.com/gene/news/news-events/lasker_award/.

Fan J B, Li SZ, Patent search report #G11102, A Chinese herb combination for treatment of macular degeneration and its preparation method. Patent Search and Consultation Center, State Intellectual Property Office of the People's Republic of China. Apr. 20, 2011.

Liu XJ, Gong YY, et al. Protective effects of pretreatment with drug serum of "Huangban granule" on hypoxic injury of human retinal pigment epithelial cells. Acta Universitatis Traditionis Medicalis Senansis Pharmacologiaeque Shanghai. Sep. 2010; 24(5):73-76.

Department of Chinese Herbal Medicine, Chinese Herbology and Its Formulas. pp. 156, 180-181, 194, 358, 361-363, 540, 542, Shandong People's Press, Jinan, 1976.

Cai YM, Wang L. Pharmacology of Chinese Herbal Medicine and Its Clinical Applications. pp. 28, 31, 52, 79, 188-189, 191, 280, 303, 313, 430, 463, 481, 483, 503, 517, Huaxia Press, Beijing, 1999.

Mei QX, Modern Pharmacology of Chinese Herbal Medicine and Clinical Applications. pp. 76, 111, 113, 166, 233, 580, 725, 726, 869, 916, China TCM Press, Beijing 2008.

Shen YJ et al. Pharmacology of Traditional Chinese Medicine. pp. 151, 203, 435, 454, 637, 638, 667, 668, 882, 924, 951, 1013, People's Health Press, Beijing 2000.

Tao MX, Zhao ZL, The protective effect of polysaccharide of *Lycium barbarum* on genetic damages induced by 2 compounds in vitro. Chinese J. Pharmacology and Toxicology, 1992; 6 (2):136.

Wen RL, Han M. The effects of Lycii fructus on DNA repair and aging. Shanxi Traditional Chinese Medicine. 2000; 16(5): 52-53. (in Chinese).

Yance, Donald R. et al. Tageting Angiogenesis with Integrative Cancer Therapies. 5(1); 2006 pp. 9-29.

Parekh HS, Liu G, et al. A new dawn for the use of traditional Chinese medicine in cancer therapy. Molecular Cancer 2009, 8:21 doi:10. 1186/1476-4598-8-21.

International Search Report, mailing date Jul. 24, 2012, for corresponding International Application No. PCT/US2012/036407.

Written Opinion of International Searching Authority, mailing date Jul. 24, 2012, for corresponding International Application No. PCT/US2012/036407.

'Tian Wang Bu Xin Wan (Pian)' http://www.activeherb.com/tianwang (htt://web.archive.org/web/20050402035139/http://www.activeherb.com/tianwang).

Notice of First Examination Comments with English translation, mailing date Mar. 2, 2012, for corresponding China Application No. 201110117394.5.

Notice of Allowance of Patent Right with English translation, mailing date Jun. 15, 2012, for corresponding China Application No. 201110117394.5.

\* cited by examiner

CHINESE HERBAL COMPOSITION FOR THE TREATMENT OF MACULAR DEGENERATION AND THE PROCESS FOR MANUFACTURING THE SAME

CROSS-REFERENCE TO RELATED APPLICATION

This application claims foreign priority under 35 U.S.C. §119 to Chinese Patent Application no. 201110117394.5, filed in the People's Republic of China on May 6, 2011, the entire contents of which are hereby incorporated by reference.

FIELD OF THE INVENTION

The present invention is generally related to a Chinese herb composition and its preparation method. Particularly, this invention relates to a Chinese herb powder composition for the treatment of macular degeneration and a preparation method of said composition.

BACKGROUND

The retina is a thin layer of neural tissue lining the back inner surface of the eye. This layer mainly consists of five types of neurons: photoreceptors, i.e. cones and rods, horizontal cells, bipolar cells, amacrine cells, and ganglion cells. The macula is the small, central portion of the retina, which comprises cones only. Such a unique structure enables the macula to provide the clearest, most distinct vision. On the other hand, it makes the macula vulnerable to degeneration due to the lack of blood vessels in this little area.

Macular degeneration is categorized into three types: Age-related macular degeneration (AMD), Myopic Macular Degeneration (MMD), and Juvenile macular degeneration or Stargardt's disease.

AMD is the leading cause of vision impairment and blindness in the elderly over 50 years of age in developed countries. AMD usually occurs in people aged 50 and older and is the most common macular degeneration. MMD is associated with high myopia. Juvenile macular degeneration is a hereditary ocular disease affecting over 25,000 Americans, occurring in approximately one in 10,000 children.

Demographic changes in population and longer life expectancy in many countries are now causing a rapid increase in the number of AMD patients. AMD has a tremendous impact on the physical and mental health of the geriatric population and their families. The cost to society should not be ignored, either. A recent analysis of AMD in Australia predicts that the disease costs $2.6 billion per year. This is projected to grow to $6.5 billion by 2025, a total cost of $59 billion over the next 20 years. A treatment that reduces the progression by only 10% would save Australia $5.7 billion over that same period of time. Similar analyses for the United States are lacking, but given the demographics and higher costs of medical care in the US, the costs would be projected to as much as twenty-fold higher.

The pathogenesis of AMD has not been fully elucidated. While many unanswered questions remain, some contributing factors have been exposed including: aging; retinal ischemia or oxidative stress; long-term exposure to intense light especially blue light; toxification by cigarette smoke, possibly alcohol consumption and some medications; hypertension, high blood cholesterol and triglycerides, which may impede blood circulation; high blood fibrinogen which helps blood clotting; and supper oxidation.

AMD can be manifested in two forms: dry AMD and wet AMD. Dry AMD accounts for 90% of cases, and wet AMD, 10%. Severe vision loss is typically associated with wet AMD but up to 20% of legal blindness from AMD is due to the dry form.

1. The pathologic changes of dry AMD: (1) Apoptosis: this process is associated with neurodegeneration including macular degeneration, leading to cell shrinkage and death in the inner choroid, RPE, photoreceptors, bipolar cells, and amacrine cells. (2) Capillaries in choroid are thinned and sclerosed. (3) Nodular drusen, observed as yellowish white spots by ophthalmoscope, are possibly from the lipoidal degeneration of RPE cells. But inflammation may also be involved in their formation. (4) Scar formation: The spaces left by the dead cells seem to be filled by the enlarged adjacent cells or by scar tissue, which will cause the retinal surface to be uneven and further visual impairment when the scars contract. (5) Geographic atrophy is characterized by an area of well demarcated atrophy of RPE, representing the classic picture of end stage dry AMD.

2. The pathologic changes of wet AMD: (1) Choroidal neovascularization (CNV), the hallmark of the wet AMD, represents the new blood vessel formation from the choroid. CNV can extend from the choroid to the space under RPE and further to the space between the RPE and the retina. (2) Hemorrhage and exudates: Since the new blood vessels are leaky, as a result, the blood and liquid ooze out, forming serous or hemorrhagic detachment of the RPE. (3) Inflammation has been reported to exist in the wet AMD process. (4) Scar formation: This is the same as in dry AMD but the scars can be a lot more severe, forming a disciform scar, representing the end stage of the wet AMD.

Myopic macular degeneration (MMD), caused by high myopia, is more prevalent than AMD in China. MMD has been the first major cause of new blindness registered in 2001-2009 in Shanghai, China. The pathology of MMD are similar in many aspects with that of AMD. The changes are mostly atrophic in nature.

1) The choroid presents atrophic changes. The capillaries become thinned and sclerosed. There are less pigments and elastin.
2) Lacquer cracks: The Bruch's membrane—pigment epithelium-choroiocapilaris complex gets stretched and ruptured which is termed as lacquer cracks.
3) The RPE cells changed in shape and there is pigment proliferation, which forms black conglomerate masses in or around the macula called Fuch's spots.
4) Formation of CNV occurs in some MMD the same as in the wet AMD.
5) Leakage and hemorrhage may happen due to the CNV in some cases or due to the Lacquer cracks in other cases without CNV.
6) Rods and cones in the retina are atrophied.

The treatment of macular degeneration has been an ongoing topic of ocular research studies in recent decades. Some important progress has been achieved in western medicinal treatments.

1. Laser photocoagulation was approved by the US FDA in 1991 for wet AMD. This treatment uses hot laser radiation to coagulate retinal new blood vessels around the macula (not for those in the center of the macula) and stops bleeding, but this procedure causes damage to the normal retina, leading to scar tissue and permanent visual impairment. Moreover, it does not prevent the new blood vessels from forming again.
2. Photodynamic therapy (PDT) was approved in 2000 by the US FDA for wet AMD, and employs cool (low energy)

laser and a light-sensitive chemical-verteporfin (Visudyne®) to destroy choroidal new blood vessels without damaging normal tissue. The PDT not only limits vision loss in wet AMD but can also significantly improve vision for 5.6% of wet AMD cases (add 3 log lines or more). Using PDT as the first-line treatment has saved the vision of hundreds of thousands of people afflicted with wet AMD. Therefore, in 2002 Dr. David Dolphin, along with Julia Levy, was awarded the Prix Galien, the highest award the American Chemical Society gives to an industrial chemist, for the discovery, development, and commercialization of Visudyne®. Although the PDT therapy has been in recent years replaced by vascular epithelial growth factor (VEGF) inhibitors as the first-line treatment, it may still play a role in combination procedures.

3. VEGF inhibitors for wet AMD. Currently, there are mainly four anti-VEGF agents that are available for clinical use: Pegaptanib (brand name Macugen®, Eyetech Pharmaceuticals Inc., New York, USA), Ranibizumab (Lucentis®, Genentech Inc., California, USA), Bevacizumab (Avastin®, Genentech Inc., California, USA) and VEGF trap-eye (also known as Eylea®, Regeneron Pharmaceuticals, Inc. N.Y.)
  1) Pegaptanib was approved by the US FDA in 2004, and is the first anti-VEGF agent for wet AMD. Its efficacy was demonstrated in the phase III clinical trial. Six percent of the patients in the treatment group gained 3 lines or more visual acuity (VA) as compared with two percent in the sham-injection group.
  2) Ranibizumab was approved by the US FDA in 2006 and is the first treatment for neovascular AMD to improve vision for most patients. In the phase III clinical trial approximately 25-33% of the patients treated with ranibizumab gained 3 lines or more in visual acuity (VA), as compared with 5% or less in the sham injection group at 12 and 24 months.
    The serious ocular events, associated with either the drug or its intraocular injection procedures, included endophthalmitis, uveitis, retinal tear, rhegmatogenous retinal detachment, vitreous hemorrhage, and lens damage, with a total event number of 21 out of 477 patients (4.4%). The elevated postinjection intraocular pressure occurred at 15.9-20.5% in the Ranibizumab-treated group, as compared with 3.4% in the sham-injection group.
  2) Bevacizumab was approved by the US FDA in 2004 for colorectal cancer treatment. However, given its lower cost, it has been widely used off-label for wet AMD in many countries. Its effectiveness was shown to be similar to that of Ranibizumab while Bevacizumab was linked to a higher risk of adverse events.
  3) VEGF trap-eye was approved by the US FDA in 2011 for wet AMD. The clinical trial results showed about 30% of the patients gained 3 lines or more in visual acuity during the study in both VEGF trap-eye group and the Ranibizumab group. Adverse effects also did not differ markedly between the two groups.

Scientists and ophthalmologists believe that the introduction of anti-VEGF agents is a major advancement and a true revolution in the history of wet macular degeneration treatment. The leader of this revolution, Napoleone Ferrara, a scientist from Genentech Inc., won the 2010 Lasker award, one of the most respected science prizes in the world, for the discovery of VEGF and the development of anti-VEGF therapy for wet AMD.

Chinese herbal medicine treatment for vision problems has been used for more than 400 years in China. However, ancient traditional Chinese medicine (TCM) practitioners had no way to distinguish what herbs were effective for macular degeneration since there had been no concept of macula at that time. Modern TCM doctors, educated with basic western medicine knowledge as part of their curriculum, have been able to know the existence of edema, bleeding, etc. in the troubled macula. When prescribing herbs based on the TCM principles, they also add herbs against those pathologic changes to improve the outcome of the treatment. This kind of prescription, however, is highly individualized and, therefore, not many clinically tested formulas are available for general use on the market.

Accordingly, there is a need for new treatments for both dry and wet macular degeneration which have a higher efficacy and lower risks. Such need is met by the use of Chinese herb compositions of the present invention.

SUMMARY OF THE INVENTION

A goal of the present invention is to provide a Chinese herb composition for all types of macular degenerations with minimum risk, thereby solving the problems of currently available drugs that are effective only for wet macular degenerations with higher risk. Another goal of the present invention is to provide a preparation method of the Chinese herb composition for the treatment of macular degeneration.

A first embodiment of the present invention comprises *Salviae miltiorrhizae, Lycii fructus, Chrysanthemi flos, Schisandrae chinensis fructus*, and *Rehmanniae radix praeparata*.

In an implementation of this embodiment, the range of units by weight for each herb component is as follows: *Salviae miltiorrhizae* 0.8-3.0 units, *Lycii fructus* 0.6-2.4 units *Chrysanthemi flos* 0.5-2.0 units, *Schisandrae chinensis fructus* 0.2-1.2 units, and *Rehmanniae radix praeparata* 0.7-3.0 units, respectively.

In another implementation of the first embodiment, the number of units by weight for each herb component is as follows: *Salviae miltiorrhizae* 2.0 units, *Lycii fructus* 2.0 units *Chrysanthemi flos* 1.0 units, *Schisandrae chinensis fructus* 0.8 units, and *Rehmanniae radix praeparata* 2.0 units, respectively.

A second embodiment of the present invention comprises *Salviae miltiorrhizae, Chuanxiong rhizoma, Lycii fructus, Chrysanthemi flos, Schisandrae chinensis fructus, Imperatae rhizoma*, and *Scutellariae radix*, where the range of units by weight for each herb component is as follows: *Salviae miltiorrhizae* 0.8-3.0 units, *Chuanxiong rhizoma* 0.3-2.0 units, *Lycii fructus* 0.6-2.4 units, *Chrysanthemi floss* 0.5-2.0 units, *Schisandrae chinensis fructus* 0.2-1.2 units, *Imperatae rhizoma* 0.9-6.0 units, and *Scutellariae radix* 0.5-2.0 units respectively.

In an implementation of the second embodiment, the number of units by weight for each herb component is as follows: *Salviae miltiorrhizae* 2.0 units, *Chuanxiong rhizoma* 1.0 units, *Lycii fructus* 2.0 units, *Chrysanthemi flos* 0.5 units, *Schisandrae chinensis fructus* 1.0 units, *Imperatae rhizoma* 2.0 units, and *Scutellariae radix* 1.0 units, respectively. In yet another implementation, the number of units by weight for each component is as follows: *Salviae miltiorrhizae* 1.0 units, *Chuanxiong rhizoma* 1.2 units, *Lycii fructus* 1.0 units *Chrysanthemi flos* 1.3 units, *Schisandrae chinensis fructus* 0.5 units, *Imperatae rhizoma* 3.0 units, and *Scutellariae radix* 2.0 units, respectively.

In another implementation of the second embodiment, the number of units by weight for each herb component is as follows: *Salviae miltiorrhizae* 1.0 units, *Chuanxiong rhizoma*

1.2 units, *Lycii fructus* 1.0 units, *Chrysanthemi flos* 1.3 units, *Schisandrae chinensis fructus* 0.5 units, *Imperatae rhizoma* 3.0 units, and *Scutellariae radix* 2.0 units, respectively.

In a third embodiment of the present invention, the Chinese herb composition for the treatment of macular degeneration comprises *Salviae miltiorrhizae, Chuanxiong rhizoma, Lycii fructus, Chrysanthemi flos, Schisandrae chinensis fructus, Imperatae rhizoma, Scutellariae radix, Rehmanniae radix praeparata, Angelicae sinensis radix, Astragali radix, Dendrobii caulis, Cassiae semen seed, Plantaginis semen, Alismatis rhizoma, Forsythiae fructus, Puerariae lobatae radix, Poria,* and *Dipsaci radix,* wherein the range of units by weight for each herb component is as follows: *Salviae miltiorrhizae* 0.8-3.0 units, *Chuanxiong rhizoma* 0.3-2.0 units, *Lycii fructus* 0.6-2.4 units, *Chrysanthemi flos* 0.5-2.0 units *Schisandrae chinensis fructus* 0.2-1.2 units, *Imperatae rhizoma* 0.9-6.0 units, *Scutellariae radix* 0.5-2.0 units, *Rehmanniae radix praeparata* 0.7-3.0 units, *Angelicae sinensis radix* 0.4-2.4 units, *Astragali radix* 0.6-6.0 units, *Dendrobii caulis* 0.6-2.4 units, *Cassiae semen* 0.9-3.0 units, *Plantaginis semen* 0.6-3.0 units, *Alismatis rhizoma* 0.4-1.8 units, *Forsythiae fructus* 0.4-3.0 units, *Puerariae lobatae radix* 0.8-3.0 units, *Poria* 0.5-3.0 units, and *Dipsaci radix* 0.7-3.0 units, respectively.

In an implementation of the third embodiment, the number of units by weight for each herb component is: *Salviae miltiorrhizae* 2.0 units, *Chuanxiong rhizoma* 1.0 units, *Lycii fructus* 2.0 units, *Chrysanthemi flos* 1.0 units, *Schisandrae chinensis fructus* 1.0 units *Imperatae rhizoma* 2.0 units, *Scutellariae radix* 1.0 units, *Rehmanniae radix praeparata* 2.0 units, *Angelicae sinensis radix* 1.0 units, *Astragali radix* 2.0 units, *Dendrobii caulis* 2.0 units *Cassiae semen* 2.0 units, *Plantaginis semen* 2.0 units, *Alismatis rhizoma* 1.3 units, *Forsythiae fructus* 1.3 units, *Puerariae lobatae radix* 2.0 units, *Poria* 2.0 units, and *Dipsaci radix* 2.0 units, respectively.

In another implementation of the third embodiment, the number of units by weight for each herb component is as follows: *Salviae miltiorrhizae* 2.3 units, *Chuanxiong rhizoma* 1.5 units, *Lycii fructus* 1.5 units, *Chrysanthemi floss* 0.6 units, *Schisandrae chinensis fructus* 0.8 units, *Imperatae rhizoma* 4.0 units, *Scutellariae radix* 1.5 units, *Rehmanniae radix praeparata* 1.7 units, *Angelicae sinensis radix* 0.7 units, *Astragali radix* 4.0 units, *Dendrobii caulis* 1.2 units, *Cassiae semen* 2.2 units, *Plantaginis semen* 2.7 units, *Alismatis rhizoma* 1.5 units *Forsythiae fructus* 2.6 units, *Puerariae lobatae radix* 1.2 units, *Poria* 2.5 units, and *Dipsaci radix* units 1.0, respectively.

In yet another implementation of the third embodiment, the number of units by weight for each herb component is as follows: *Salviae miltiorrhizae* 1.0 units, *Chuanxiong rhizoma* 0.8 units, *Lycii fructus* 1.0 units, *Chrysanthemi flos* 1.5 units, *Schisandrae chinensis fructus* 0.5 units, *Imperatae rhizoma* 2.5 units, *Scutellariae radix* 2.0 units, *Rehmanniae radix praeparata* 2.4 units, *Angelicae sinensis radix* 1.5 units, *Astragali radix* 1.4 units, *Dendrobii caulis* 1.0 units, *Cassiae semen* 1.3 units, *Plantaginis semen* 2.2 units, *Alismatis rhizoma* 1.7 units, *Forsythiae fructus* 1.5 units, *Puerariae lobatae radix* 2.5 units, *Poria* 2.7 units, and Dipsaci radix 2.7 units, respectively.

A fourth embodiment of the present invention provides a Chinese herb composition for the treatment of macular degeneration, comprising: *Salviae miltiorrhizae, Chuanxiong rhizoma, Lycii fructus, Chrysanthemi flos, Schisandrae chinensis fructus, Imperatae rhizoma, Scutellariae radix, Rehmanniae radix praeparata, Angelicae sinensis radix, Astragali radix, Dendrobii caulis, Cassiae semen seed, Plantaginis semen, Alismatis rhizoma, Forsythiae fructus, Puerariae lobatae radix, Poria, Dipsaci radix* and *Silybi fructus* or Silybin, where the range of units by weight for each component is as follows: *Salviae miltiorrhizae* 0.8-3.0 units *Chuanxiong rhizoma* 0.3-2.0 units, *Lycii fructus* 0.6-2.4 units, *Chrysanthemi floss* 0.5-2.0 units, *Schisandrae chinensis fructus* 0.2-1.2 units, *Imperatae rhizoma* 0.9-6.0 units *Scutellariae radix* 0.5-2.0 units, *Rehmanniae radix praeparata* 0.7-3.0 units, *Angelicae sinensis radix* 0.4-2.4 units, *Astragali radix* units 0.6-6.0, *Dendrobii caulis* 0.6-2.4 units, *Cassiae semen* 0.9-3.0 units, *Plantaginis semen* 0.6-3.0 units, *Alismatis rhizoma* 0.4-1.8 units *Forsythiae fructus* 0.4-3.0 units, *Puerariae lobatae radix* 0.8-3.0 units, *Poria* 0.5-3.0 units *Dipsaci radix* 0.7-3.0 units, and *Silybi fructus* 0.5-3.0 units, respectively. In an alternative embodiment, the *Silybi fructus* is replaced with Silybin of 0.035-0.14 units.

In an implementation of the fourth embodiment, the Chinese herb composition for the treatment of macular degeneration has a number of units by weight for each herb component as follows: *Salviae miltiorrhizae* 2.3 units, *Chuanxiong rhizoma* 1.5 units, *Lycii fructus* 1.5 units, *Chrysanthemi floss* 0.6 units, *Schisandrae chinensis fructus* 0.8 units, *Imperatae rhizoma* 4.0 units, *Scutellariae radix* 1.5 units, *Rehmanniae radix praeparata* 1.7 units *Angelicae sinensis radix* 0.7 units, *Astragali radix* 4.0 units, *Dendrobii caulis* 1.2 units *Cassiae semen* 2.2 units, *Plantaginis semen* 2.7 units, *Alismatis rhizoma* 1.5 units, *Forsythiae fructus* 2.6 units, *Puerariae lobatae radix* 1.2 units, *Poria* 2.5 units, *Dipsaci radix* 1.0 units and *Silybi fructus* 1.0 units or *Silybin* 0.07 units, respectively.

In another implementation of the fourth embodiment, the Chinese herb composition for the treatment of macular degeneration has a number of units by weight for each herb component as follows: *Salviae miltiorrhizae* 1.0 units, *Chuanxiong rhizoma* 0.8 units, *Lycii fructus* 1.0 units, *Chrysanthemi floss* 1.5 units, *Schisandrae chinensis fructus* 0.5 units *Imperatae rhizoma* 2.5 units, *Scutellariae radix* 2.0 units, *Rehmanniae radix praeparata* 2.4 units, *Angelicae sinensis radix* 1.5 units, *Astragali radix* 1.4 units, *Dendrobii caulis* 1.0 units *Cassiae semen* 1.3 units, *Plantaginis semen* 2.2 units, *Alismatis rhizoma* 1.7 units, *Forsythiae fructus* 1.5 units, *Puerariae lobatae radix* 2.5 units, *Poria* 2.7 units, *Dipsaci radix* 2.7 units and *Silybi fructus* 2.0 units or *Silybin* 0.14 units, respectively.

The present invention also provides a method for preparing the compositions for treating macular degeneration. According to an embodiment, this method comprises the steps of: obtaining a five-fold concentrated powder of herb extract for each herb component according to said number of units by weight; and evenly mixing all of said concentrated powders to form a mixed powder composition. The mixed powder composition is further prepared by placing into a form selected from the group consisting of, but not limited to, tablets, pills, granulates, pellets, capsules, paper bags and plastic bags, solid mixtures, dispersions in liquid phases, suspensions, emulsions, solutions and pastes. The composition may be administered orally or parenterally in a clinically acceptable dosage and form.

These features, advantages and other embodiments of the present invention are further made apparent, in the remainder of the present document, to those of ordinary skill in the art.

DETAILED DESCRIPTION OF SPECIFIC EMBODIMENTS

The present invention provides a Chinese herb composition for the treatment of macular degeneration. While the present invention may be embodied in many different formulas for the purpose of promoting an understanding of the principles of the invention, it will nevertheless be understood that no limitation or restriction of the scope of the invention is thereby intended. Any alterations and further implementations of the principles of the invention as described herein are contemplated as would normally occur to one skilled in the art to which the invention relates.

Given the heterogeneous nature of this eye disease, a comprehensive approach was utilized in this invention. In addition to the TCM differentiation of syndromes and treatment principles, modern knowledge on the disease was adapted to collect as many contributing factors and pathological changes as possible, including the hidden underlying conditions as well as the possible future conditions as treatment targets. Meanwhile, modern knowledge on herb pharmacology was implemented as a guide for herb selection to attack the targets chosen above. It is intended that a full range of intervention would render better results than a narrow-angled one does.

A first embodiment of the present invention provides for a Chinese herb composition for the treatment of macular degeneration, which is mainly comprised of Salviae miltiorrhizae, Lycii fructus, Chrysanthemi flos, Schisandrae chinensis fructus, and Rehmanniae radix praeparata. In a particular implementation of this embodiment, the range of units by weight for each component is as follows: *Salviae miltiorrhizae* 0.8-3.0 units, *Lycii fructus* 0.6-2.4 units, *Chrysanthemi flos* 0.5-2.0 units, *Schisandrae chinensis fructus* 0.2-1.2 units, and Rehmanniae radix praeparata 0.7-3.0 units, respectively.

In another implementation of the first embodiment of the present invention, as further shown in Table 1, there is provided a Chinese herb composition for the treatment of macular degeneration comprising by units of weight: *Salviae miltiorrhizae* 2.0 units, *Lycii fructus* 2.0 units, *Chrysanthemi flos* 1.0 units, *Schisandrae chinensis fructus* 0.8 units, and Rehmanniae radix praeparata 2.0 units.

TABLE 1

| Name | Amount (g)* | Name | Amount (g)* |
|---|---|---|---|
| Salviae miltiorrhizae | 2.0 | Lycii fructus | 2.0 |
| Chrysanthemi flos | 1.0 | Schisandrae chinensis fructus | 0.8 |
| Rehmanniae radix praeparata | 2.0 | | |

*5-fold concentrated powder of extract

A second embodiment of the present invention, provides a Chinese herb composition for the treatment of macular degeneration, which mainly comprises *Salviae miltiorrhizae, Chuanxiong rhizoma, Lycii fructus, Chrysanthemi flos, Schisandrae chinensis fructus, Imperatae rhizoma,* and *Scutellariae radix*. In an implementation of this second embodiment, the range of units by weight for each component is as follows: *Salviae miltiorrhizae* 0.8-3.0 units, *Chuanxiong rhizoma* 0.3-2.0 units, *Lycii fructus* 0.6-2.4 units, *Chrysanthemi floss* 0.5-2.0 units, *Schisandrae chinensis fructus* 0.2-1.2 units, *Imperatae rhizoma* 0.9-6.0 units, and *Scutellariae radix* 0.5-2.0 units, respectively.

In another implementation according to the second embodiment, the components and its number of units by weight include: *Salviae miltiorrhizae* 2.0 units, *Chuanxiong rhizoma* 1.0 units, *Lycii fructus* 2.0 units, *Chrysanthemi flos* 0.5 units, *Schisandrae chinensis fructus* 1.0 units, *Imperatae rhizoma* 2.0 units, and *Scutellariae radix* 1.0 units.

In a further implementation according to the second embodiment, the components and its number of units by weight include: *Salviae miltiorrhizae* 1.0 units, *Chuanxiong rhizoma* 1.2 units, *Lycii fructus* 1.0 units, *Chrysanthemi flos* 1.3 units, *Schisandrae chinensis fructus* 0.5 units, *Imperatae rhizoma* 3.0 units, and *Scutellariae radix* 2.0 units.

A third embodiment of the present invention provides a Chinese herb composition for the treatment of macular degeneration, which mainly comprises *Salviae miltiorrhizae, Chuanxiong rhizoma, Lycii fructus, Chrysanthemi flos, Schisandrae chinensis fructus, Imperatae rhizoma, Scutellariae radix, Rehmanniae radix praeparata, Angelicae sinensis radix, Astragali radix, Dendrobii caulis,* Cassiae semen seed, Plantaginis semen, Alismatis rhizoma, Forsythiae fructus, Puerariae lobatae radix, Poria, and *Dipsaci radix*.

In an implementation of the third embodiment, the range of units by weight for each component is as follows: *Salviae miltiorrhizae* 0.8-3.0 units, *Chuanxiong rhizoma* 0.3-2.0 units, *Lycii fructus* 0.6-2.4 units, *Chrysanthemi flos* 0.5-2.0 units, *Schisandrae chinensis fructus* 0.2-1.2 units, *Imperatae rhizoma* 0.9-6.0 units, *Scutellariae radix* 0.5-2.0 units *Rehmanniae radix praeparata* 0.7-3.0 units, *Angelicae sinensis radix* 0.4-2.4 units, *Astragali radix* 0.6-6.0 units, *Dendrobii caulis* 0.6-2.4 units, *Cassiae semen* 0.9-3.0 units, *Plantaginis semen* 0.6-3.0 units, *Alismatis rhizoma* 0.4-1.8 units, *Forsythiae fructus* 0.4-3.0 units *Puerariae lobatae radix* 0.8-3.0 units, *Poria* 0.5-3.0 units, and *Dipsaci radix* 0.7-3.0 units.

In another implementation of the third embodiment, and as set forth in Table 2 below, the number of units by weight for each component is: *Salviae miltiorrhizae* 2.0 units *Chuanxiong rhizoma* 1.0 units, *Lycii fructus* 2.0 units, *Chrysanthemi flos* 1.0 units *Schisandrae chinensis fructus* 1.0 units, *Imperatae rhizoma* 2.0 units, *Scutellariae radix* 1.0 units, *Rehmanniae radix praeparata* 2.0 units, *Angelicae sinensis radix* 1.0 units, *Astragali radix* 2.0 units, *Dendrobii caulis* 2.0 units, *Cassiae semen* 2.0 units, *Plantaginis semen* 2.0 units, *Alismatis rhizoma* 1.3 units, *Forsythiae fructus* 1.3 units, *Puerariae lobatae radix* 2.0 units, *Poria* 2.0 units, and *Dipsaci radix* 2.0 units, respectively.

TABLE 2

| Name | Amount (g)* | Name | Amount (g)* |
|---|---|---|---|
| Rehmanniae radix praeparata | 2.0 | Schisandrae chinensis fructus | 1.0 |
| Angelicae sinensis radix | 1.0 | Astragali radix | 2.0 |
| Chuanxiong rhizoma | 1.0 | Dendrobii caulis | 2.0 |
| Cassiae semen | 2.0 | Imperatae rhizoma | 2.0 |
| Chrysanthemi flos | 1.0 | Plantaginis semen | 2.0 |
| Lycii fructus | 2.0 | Alismatis rhizoma | 1.3 |
| Salviae miltiorrhizae | 2.0 | Forsythiae fructus | 1.3 |
| Puerariae lobatiae radix | 2.0 | Poria | 2.0 |
| Dipsaci radix | 2.0 | Scutellariae radix | 1.0 |

*5-fold concentrated powder of extract

In a further implementation of the third embodiment, the number of units by weight for each component is: *Salviae miltiorrhizae* 2.3 units, *Chuanxiong rhizoma* 1.5 units, *Lycii fructus* 1.5 units, *Chrysanthemi floss* 0.6 units, *Schisandrae chinensis fructus* 0.8 units *Imperatae rhizoma* 4.0 units, *Scutellariae radix* 1.5 units, *Rehmanniae radix praeparata* 1.7 units, *Angelicae sinensis radix* 0.7 units, *Astragali radix* 4.0 units, *Dendrobii caulis* 1.2 units *Cassiae semen* 2.2 units, *Plantaginis semen* 2.7 units, *Alismatis rhizoma* 1.5 units, *Forsythiae fructus* 2.6 units, *Puerariae lobatae radix* 1.2 units, *Poria* 2.5 units, and *Dipsaci radix* units 1.0, respectively.

In another implementation of the third embodiment, the components and its number of units by weight include:

Salviae miltiorrhizae 1.0 units, Chuanxiong rhizoma 0.8 units, Lycii fructus 1.0 units, Chrysanthemi flos 1.5 units, Schisandrae chinensis fructus 0.5 units Imperatae rhizoma 2.5 units, Scutellariae radix 2.0 units, Rehmanniae radix praeparata 2.4 units, Angelicae sinensis radix 1.5 units, Astragali radix 1.4 units, Dendrobii caulis 1.0 units Cassiae semen 1.3 units, Plantaginis semen 2.2 units, Alismatis rhizoma 1.7 units, Forsythiae fructus 1.5 units, Puerariae lobatae radix 2.5 units, Poria 2.7 units, and Dipsaci radix 2.7 units.

A fourth embodiment of the present invention provides a Chinese herb composition for the treatment of macular degeneration, which mainly comprises *Salviae miltiorrhizae, Chuanxiong rhizoma, Lycii fructus, Chrysanthemi flos, Schisandrae chinensis fructus, Imperatae rhizoma, Scutellariae radix, Rehmanniae radix praeparata, Angelicae sinensis radix, Astragali radix, Dendrobii caulis, Cassiae semen seed, Plantaginis semen, Alismatis rhizoma, Forsythiae fructus, Puerariae lobatae radix, Poria, Dipsaci radix* and *Silybi fructus* or alternatively *Silybin*.

In this fourth embodiment, the range of units by weight for each component is: Salviae miltiorrhizae 0.8-3.0 units, Chuanxiong rhizoma 0.3-2.0 units, Lycii fructus 0.6-2.4 units Chrysanthemi floss 0.5-2.0 units, Schisandrae chinensis fructus 0.2-1.2 units, Imperatae rhizoma 0.9-6.0 units, Scutellariae radix 0.5-2.0 units, Rehmanniae radix praeparata 0.7-3.0 units, Angelicae sinensis radix 0.4-2.4 units, Astragali radix 0.6-6.0 units, Dendrobii caulis 0.6-2.4 units, Cassiae semen 0.9-3.0 units, Plantaginis semen 0.6-3.0 units, Alismatis rhizoma 0.4-1.8 units, Forsythiae fructus 0.4-3.0 units, Puerariae lobatae radix 0.8-3.0 units, Poria 0.5-3.0 units, Dipsaci radix 0.7-3.0 units, and Silybi fructus 0.5-3.0 units or alternatively Silybin 0.035-0.14 units, respectively.

In one implementation of the fourth embodiment, and as set forth in Table 3, the number of units by weight of each component is: Salviae miltiorrhizae 2.0 units, Chuanxiong rhizoma 1.0 units, Lycii fructus 2.0 units, Chrysanthemi flos 1.0 units, Schisandrae chinensis fructus 1.0 units, Imperatae rhizoma 2.0 units, Scutellariae radix 1.0 units, Rehmanniae radix praeparata 2.0 units, Angelicae sinensis radix 1.0 units, Astragali radix 2.0 units, Dendrobii caulis 2.0 units, Cassiae semen 2.0 units, Plantaginis semen 2.0 units, Alismatis rhizoma 1.3 units, Forsythiae fructus 1.3 units, Puerariae lobatae radix 2.0 units, Poria 2.0 units, Dipsaci radix 2.0 units, and Silybi fructus 0.5 units, respectively.

TABLE 3

| Name | Amount (g)* | Name | Amount (g)* |
|---|---|---|---|
| Rehmanniae radix praeparata | 2.0 | Schisandrae chinensis fructus | 1.0 |
| Angelicae sinensis radix | 1.0 | Astragali radix | 2.0 |
| Chuanxiong rhizoma | 1.0 | Dendrobii caulis | 2.0 |
| Cassiae semen | 2.0 | Imperatae rhizoma | 2.0 |
| Chrysanthemi flos | 1.0 | Plantaginis semen | 2.0 |
| Lycii fructus | 2.0 | Alismatis rhizoma | 1.3 |
| Salviae miltiorrhizae | 2.0 | Forsythiae fructus | 1.3 |
| Puerariae lobatiae radix | 2.0 | Poria | 2.0 |
| Dipsaci radix | 2.0 | Scutellariae radix | 1.0 |
| Silybi fructus | 0.5 | | |

*5-fold concentrated powder of extract

In an alternative implementation according to this fourth embodiment, the number of units by weight of each component is as follows: Salviae miltiorrhizae 2.0 units, Chuanxiong rhizoma 1.0 units, Lycii fructus 2.0 units, Chrysanthemi flos 1.0 units, Schisandrae chinensis fructus 1.0 units, Imperatae rhizoma 2.0 units, Scutellariae radix 1.0 units, Rehmanniae radix praeparata 2.0 units, Angelicae sinensis radix 1.0 units, Astragali radix 2.0 units, Dendrobii caulis 2.0 units, Cassiae semen 2.0 units, Plantaginis semen 2.0 units, Alismatis rhizoma 1.3 units, Forsythiae fructus 1.3 units, Puerariae lobatae radix 2.0 units, Poria 2.0 units, Dipsaci radix 2.0 units, and Silybin 0.035 units, respectively.

In a further implementation according to this fourth embodiment, the number of units by weight for each component is as follows: Salviae miltiorrhizae 2.3 units, Chuanxiong rhizoma 1.5 units, Lycii fructus 1.5 units, Chrysanthemi floss 0.6 units, Schisandrae chinensis fructus 0.8 units, Imperatae rhizoma 4.0 units, Scutellariae radix 1.5 units, Rehmanniae radix praeparata 1.7 units, Angelicae sinensis radix 0.7 units, Astragali radix 4.0 units, Dendrobii caulis 1.2 units, Cassiae semen 2.2 units, Plantaginis semen 2.7 units, Alismatis rhizoma 1.5 units, Forsythiae fructus 2.6 units, Puerariae lobatae radix 1.2 units, Poria 2.5 units, Dipsaci radix units 1.0, and Silybi fructus 1.0 units, respectively.

In an alternative implementation according to this fourth embodiment, the number of units by weight of each component is as follows: Salviae miltiorrhizae 2.3 units, Chuanxiong rhizoma 1.5 units, Lycii fructus 1.5 units, Chrysanthemi floss 0.6 units, Schisandrae chinensis fructus 0.8 units, Imperatae rhizoma 4.0 units, Scutellariae radix 1.5 units, Rehmanniae radix praeparata 1.7 units, Angelicae sinensis radix 0.7 units, Astragali radix 4.0 units, Dendrobii caulis 1.2 units, Cassiae semen 2.2 units, Plantaginis semen 2.7 units, Alismatis rhizoma 1.5 units, Forsythiae fructus 2.6 units, Puerariae lobatae radix 1.2 units, Poria 2.5 units, Dipsaci radix units 1.0, and Silybin 0.07 units, respectively.

In a further implementation according the fourth embodiment, the number of units by weight of each component is as follows: Salviae miltiorrhizae 1.0 units, Chuanxiong rhizoma 0.8 units, Lycii fructus 1.0 units, Chrysanthemi flos 1.5 units, Schisandrae chinensis fructus 0.5 units, Imperatae rhizoma 2.5 units, Scutellariae radix 2.0 units, Rehmanniae radix praeparata 2.4 units, Angelicae sinensis radix 1.5 units, Astragali radix 1.4 units, Dendrobii caulis 1.0 units, Cassiae semen 1.3 units, Plantaginis semen 2.2 units, Alismatis rhizoma 1.7 units, Forsythiae fructus 1.5 units, Puerariae lobatae radix 2.5 units, Poria 2.7 units, Dipsaci radix 2.7 units, and Silybi fructus 2.0 units, respectively.

In an alternative implementation according this embodiment, the components and its number of units by weight include: Salviae miltiorrhizae 1.0 units, Chuanxiong rhizoma 0.8 units, Lycii fructus 1.0 units, Chrysanthemi flos 1.5 units, Schisandrae chinensis fructus 0.5 units, Imperatae rhizoma 2.5 units, Scutellariae radix 2.0 units, Rehmanniae radix praeparata 2.4 units, Angelicae sinensis radix 1.5 units, Astragali radix 1.4 units, Dendrobii caulis 1.0 units, Cassiae semen 1.3 units, Plantaginis semen 2.2 units, Alismatis rhizoma 1.7 units Forsythiae fructus 1.5 units, Puerariae lobatae radix 2.5 units, Poria 2.7 units, Dipsaci radix 2.7 units, and Silybin 0.14 units.

Each of the Chinese herb powders are a 5-fold concentrated powder of herb extract manufactured by Mintong Pharmaceutical Inc., Taiwan.

For all the embodiments, if dried Chinese herbs or herb slices, instead of the 5-fold concentrated powder of herb extract, are used to alternatively prepare the composition for the treatment of macular degeneration, the amount of each herb component is five times the weight of the corresponding powder of herb extract as provided in the example embodiments.

The present invention also teaches a method for preparing the Chinese herb composition. According to the embodiments, the method comprises the steps of: obtaining the concentrated powder of each component according the number of units by weight; mixing all of the concentrated powders evenly; placing the mixed powder into bottles, capsules, paper bags or plastic bags, or forming the mixed powder into tablet form.

Typically, the bottles are medical plastic bottles with 100 g capacity; the capsules are No. 0 sized capsules, where each capsule contains powder of 0.5 g; or the paper bags are non-toxic medicinal paper bags, where each bag contains powder of 5.0 g; or the plastic bags are opaque, non-toxic medical plastic bags, where each plastic bag contains powder of 5.0 g; or the tablets contain the powder of 1.0 g each.

For the embodiments with five herbal components, the adult daily amount is 6 g for oral intake. The daily amount can be increased up to 11 g if the patient is overweight or if vision does not improve within the first month of treatment. For the embodiments with seven herbal components, the adult daily amount for oral intake is 7 g. The daily amount can be increased up to 14 g if the patient is overweight or if vision does not improve during the first month of treatment. For the embodiments with eighteen or nineteen components, the oral daily amount is 10 g. The daily amount can be increased up to 30 g if the patient is overweight or if there is no vision improvement during the first month of treatment. Typically, the daily amount is divided into two doses taken orally after meal. A course of treatment is two to four months.

The compositions in this invention may be prepared into different clinically acceptable dosages as well as a variety of dosage forms, which includes, but are not limited to, capsules, tablets, pills, granulates, pellets, solid mixtures, dispersions in liquid phases, suspensions, emulsions, powders, solutions and pastes. The solutions, suspensions, emulsions and pastes may be administered parenterally.

The beneficiary effects of this invention include: 1. This Chinese herb composition provides an effective treatment for wet AMD with no toxic or severe side effects; 2. This Chinese herb composition can be conveniently taken by mouth with no invasive procedures and, therefore, eliminating the possibility of any complications caused by VEGF inhibitor injections; 3. This Chinese herb composition is also effective for dry AMD, which is more common, accounting for 90% of all AMDs, and there is no effective western medicine available so far for this eye problem; 4. This Chinese herb composition is also effective for MMD and juvenile macular degeneration; 5. This Chinese herb composition is also effective for optic atrophy, for which no effective western medicine is yet available.

To explain the beneficiary effects, clinical observation data are provided as further shown herein. Using the Chinese herb composition according to the embodiment as shown in Table 1, forty-three eyes with macular degeneration from twenty-four patients were treated. All of the patients had been previously diagnosed by ophthalmologists in the US. Some had been treated with no significant effects, and some had been offered no treatment at all. Among these forty-three eyes there were seventeen eyes (39.5%) with AMD, seventeen eyes (39.5%) with MMD, nine eyes (20.9%) with juvenile macular degeneration. Moreover, of the forty-three eyes, dry macular degeneration accounts for 62.8% (twenty-seven eyes), and wet macular degeneration accounts for 37.2% (sixteen eyes).

The efficacy is categorized in four grades: "excellent" means vision increased by 3 log lines or more; "good" means vision increased by 2 log lines; "fair" means vision increased by 1 log line; and "no change" means no increase or decrease in vision.

After two to five months of treatment, among these forty-three eyes, approximately 53.5% (twenty-three eyes) had achieved excellent, 27.9% (twelve eyes) had reached good, and 18.6% (8 eyes) had met fair.

In a comparison of dry forms of macular degeneration with wet forms, among twenty-seven eyes with dry macular degeneration, about 51.9% (fourteen eyes) were excellent, 33.3% (nine eyes) were good, and 14.8% (four eyes) were fair. While among sixteen eyes with wet macular degeneration, the results were 56.3% (nine eyes) for excellent, 18.8% (three eyes) for good, and 25% (four eyes) for fair, respectively. This shows a similar efficacy between dry and wet forms of macular degeneration.

When comparing the efficacy among three types of the macular degeneration, it was found that among seventeen eyes with AMD, 35.3% (six eyes) were excellent, 23.5% (four eyes) were good, and 41.1% (seven eyes) were fair. While among seventeen eyes with MMD, the results were 58.8% (ten eyes) for excellent, 29.4% (five eyes) for good, and 11.8% (two eyes) for fair, respectively. Whereas among nine eyes with juvenile macular degeneration, the percentages were 66.6% (six eyes) for excellent, and 33.3% (three eyes) for good, respectively.

For preliminary comparison, data from different sources as summarized in Table 4, show percentages of the highest vision improvement by using different treatments. As shown, treatments from the present invention appear to be superior in comparison.

TABLE 4

Percentages of highest vision gain in macular degeneration patients with different treatments

| Source | Treatment method | Percentages of vision gain by 3 lines or more |
| --- | --- | --- |
| N Eng J Med. v2006: 355 (14): 1419-1431. | 0.5 mg Lucentis ® intraocular Injection | 33.80% |
| Zhongshan Eye Center, 2007 | Avastin ® intraocular injection + Photodynamic Therapy | 25% |
| Department of Ophthalmology, Nanjing traditional Chinese medicine hospital | Oral Chinese herb Medicine | 29.40% |
| Present invention | Oral Chinese herb composition, embodiment Table 1 | 40.70% |
| Present invention | Oral Chinese herb composition, embodiment Table 2 | 53.50% |
| Present invention | Oral Chinese herb composition, embodiment Table 3 | 54.60% |

As to severe macular degeneration patients treated with Chinese herb composition in the above-mentioned clinical observation, the percentage of eyes with baseline vision 20/200 to 20/320 was 19.4% of the eyes which had a baseline vision equal to or better than 20/320 before treatment. After treatment with the Chinese herb composition, the percentage had reduced to zero since all patients experienced vision improvement. In comparison, in the 0.3 mg Lucentis® group in phase III clinical trial, the percentage was 14.7% before treatment and had remained the same after the treatment, representing a 100% no change in the percentage. More data from different sources are summarized in Table 5.

TABLE 5

Vision improvements in severe macular degeneration patients with different treatments

| Source | Baseline condition | Treatment method | Change in vision after treatment ||||
|---|---|---|---|---|---|---|---|
| | | | Decrease | No change | Gain 1 line | Gain 2 lines | Gain 3 or more lines |
| N Eng J Med. 2006:355 (14): 1419-1431. | vision = 20/200 to 20/320 | 0.3 mg Lucentis ® injection | * | 100%** | * | * | * |
| Chin J TCM2009; 19(6):340 | Late stage | Chinese herb medicine | 20.60% | 50% gained 0 or 1 line*** || 29.4% gained 2 lines or more*** ||
| Present Invention | vision = 20/200 to 20/500 | Chinese herb powder composition embodiment Table 2 | 0% | 0% | 14.3% | 14.3% | 71.4% |

*Not provided
**No change in percentage
***It is considered as 1 line gain if the vision increases from light perception to 20/1000, or from 20/1000 to 20/400, or from 20/400 to 20/200.

In this clinical observation, the measurable vision increase started mostly after seven days of the treatment. The best results were reached from two to five months. Surprisingly, no patient experienced a decrease in vision during the treatment.

The efficacy of the present Chinese herb powder composition (embodiment of Table 2) for optic atrophy: using the same grading standard as that for macular degeneration, among thirty-five eyes with optic atrophy from twenty-two patients, the efficacy was 42.9% excellent, 22.9% good, 28.6% fair, and 5.7% no change.

To further explain the beneficiary effects of this invention based on modern research of the herbs, thirteen related pharmacological effects are described below.

1. Improving microcirculation: *Salviae miltiorrhizae, Chuanxiong rhizome, Puerariae lobatae radix*, and *Angelicae sinensis radix* can individually and together improve microcirculation and increase the blood and oxygen supply for visual cells and the retinal pigment epithelial (RPE) cells. This can prevent or reduce choroidal neovascularization since tissue oxygen deficiency is a prerequisite for the generation of new blood vessels. In addition, while the oxygen supply is increased, so is the supply of nutrients. Consequently, the macular function improves.

2. Reducing hyperlipidemia and atherosclerosis: The effects of reducing hyperlipidemia and atherosclerosis can be rendered by the following herbs: *Salviae miltiorrhizae, Scutellariae radix, Lycii fructus, Puerariae lobatae radix, Plantaginis semen, Alismatis rhizome, Chrysanthemi flos, Angelicae sinensis radix*, and *Cassiae semen*.

3. Lowering the blood pressure: Hypertension and ischemia are both contributing factors for macular degeneration. A reduction in blood pressure will improve the circulation and relieve the ischemia of the choroid and retina. All of the following herbs have such effects: *Salviae miltiorrhizae, Chuanxiong rhizoma, Scutellariae radix, Alismatis rhizoma* and *Astragali radix*.

4. Increasing cell tolerance to hypoxia: Increased tolerance to hypoxia can reduce the damage and improve the function of the hypoxic cells. The following herbs carry such an effect. *Salviae miltiorrhizae, Astragali radix, Chrysanthemi flos, Lycii fructus* and *Puerariae lobatae radix*.

5. Reducing free radicals and suppressing super oxidation: Super oxidation is an important factor that leads to cell aging and other pathologic changes. *Salviae miltiorrhizae, Astragali radix, Chrysanthemi flos, Cassiae semen, Schisandrae chinensis fructus, Puerariae lobatae radix*, and *Rehmanniae radix praeparata*, each functions against super oxidation.

6. Protecting nerves against aging, genotoxicants and apoptosis: All the following herbs have a protective function against nerve damage but each works in a different way. *Lycii fructus* can improve DNA repair function and protect genetic materials from damage by genotoxicants. In sister chromatid exchange (SCE) experiments, *Lycii fructus* significantly reduced the SCE frequency induced by Mytomycin C (MMC). In clinical trial, among 31 people over the age of 60, their SCE frequency reduced to the level similar to that for young persons. Researchers found that *Lycii fructus* improved DNA repair function and was reported to promote rejuvenation of aging cells. *Salviae miltiorrhizae* has neurotrophic and neuro-repair functions, by which this herb can protect nerves and increase hippocampus neuron survival rate in an experimental hypoxic condition; *Rehmanniae radix praeparata* can inhibit apoptosis of neurons in rat experiments; *Schisandrae chinensis fructus* can protect brain cells against apoptosis in vitro and can also enhance the protein, RNA and DNA synthesis in the neurons of the rat brain. Astragali radix prolongs the cell life span by one-third in cultured cells; *Dipsaci radix* can inhibit the formation of amyloid precursor protein in brain neurons and improves memory in the experiment with rats. In the lab research, Scutellariae radix can inhibit neuronal apoptosis in hypoxic conditions and protect the Neuro 2A cells.

7. Reducing inflammatory reactions: Inflammatory reaction exists in AMD as mentioned above. One of the manifestations of the inflammation is the increased vascular permeability, which causes leakage and hemorrhage. Thus, reducing the inflammation including the high permeability is one of the targets of the treatment. *Scutellariae radix, Salviae*

*miltiorrhizae, Chrysanthemi flos,* and *Dipsaci radix, Plantaginis semen* and *Forsythiae fructus,* all have such an effect.

8. Reducing the retinal swelling: Extra water and other exudates that come from the leaky blood vessels stay between cells, making tissue swollen. Draining away this water and exudates will help reduce the swelling and restore the retinal functions. Several herbs, such as *Poria, Alismatis rhizoma, Plantaginis semen, Scutellariae radix,* and *Astragali radix,* all function to this end.

9. Reducing the permeability of the blood vessels and stopping hemorrhage: The bleeding in macular degeneration is usually in a trace amount oozed out from the leaky blood vessels. Therefore the best way to stop the bleeding is to reduce the permeability. All the herbs with such an effect may help stop bleeding of this kind, especially, *Imperatae rhizoma, Forsythiae fructus, Chrysanthemi flos, Rehmanniae radix praeparata,* and *Dipsaci radix.*

10. Detoxification: *Forsythiae fructus* can destroy, not only inhibit, endotoxin, *Scutellariae radix* protects normal endothelium against Endotoxin, detoxifies Strychnine and Carbon tetrachloride. *Astragali radix* protects Ribonuclease from being damaged by Mercury. *Puerariae lobatae radix* increases the $LD_{50}$ of Deltamethrin and detoxifies alcohol. *Chrysanthemi flos* can help remove lead out of bones and blood. Chuanxiong rhizome can reduce the toxic effects to ears caused by Kanamycin and Cyclosporin A. Moreover, Chuanxiong rhizome was reported to reduce the acute lung damage from cigarette smoke. Although these substances except cigarettes have not been confirmed to be related to the pathogenesis of macular degeneration, these herbs may still provide some potential benefits in this aspect.

11. Preventing scar formation: If exudates and hemorrhages in the retina cannot be completely absorbed, it may lead to scar formation, resulting in a permanent loss of vision. Therefore, treatment measures against scar formation should be taken as early as possible. *Salviae miltiorrhizae* not only inhibits the collagen synthesis in culture but also activates the collagenase, which degrades existing collagen. Scutellariae radix can inhibit fibroblast proliferation and Chuanxiong rhizoma can inhibit types I and III collagen mRNA expression in cultured fibroblasts; Angelicae sinensis radix can reduce the collagen amount in a damaged rat liver; and, *Poria* can reduce the collagen amount in the experimental liver cirrhosis and increase the excreted amount of hydroxyproline (the main component of collagen) from urine, indicating the collagen degradation in the liver.

12. Inhibiting angiogenesis: Inhibition of angiogenesis helps not only control wet macular degeneration, but also prevents the deterioration of dry macular degeneration into the wet form. Recent animal experiments show that Scutellariae radix can down-regulate the VEGF-mRNA (messenger Ribonucleic Acid) expression. Silybi fructus was found in lab to induce apoptosis of endothelial cells in tumor tissue and to reduce the VEFG production in culture. It was also reported that Silybi fructus reduced human VEGF and lead to apoptosis of the endothelial cells. Based on these results, the above herbs may play a similar role in the eye with macular degeneration.

13. Protecting cells against light damage: *Scutellariae radix* has been reported to promote the recovery of cell bioactivity by 8-38% for skin squamous cells damaged by ultraviolet A and B if the cells are pretreated with this herb. Based on this result, Scutellariae radix may in a similar way help reduce the further damage from ultraviolet to the eyes with macular degeneration.

As to the side effects, one patient caught a common cold during the herb treatment with a cough and a trace of blood found in the sputum. The patient discontinued the herb until her recovery from the cold. Thereafter, the patient continued taking the herbs with no problem. Two patients found bowel movement smoother for a few days. Another patient felt too much moisture in his eyes for a couple of weeks. But it is not clear if these are all related to the herb intake.

To illustrate the beneficial effects of this Chinese herb composition, four specific yet typical cases are reported.

Case 1: Female, Chinese, in her 70s suffered from AMD for four years, during which she was under Western medicine and a premade Chinese herb medicine (Fu Fang Xue Shuan Tong) treatment and her visual acuity (VA) did not increase, but decreased from 0.5 to 0.4 on a decimal vision chart. One week after taking the Chinese herb composition according to the embodiment of the present invention (embodiment of Table 2), her VA increased from 0.4 to 0.6. After two more weeks of this herb intake, her VA was 0.8. After five more weeks, there was an increase to 0.9. After eight more weeks, there was an increase to 1.0. The increase from 0.4 to 1.0 equals 4 log lines. After another eight more weeks her VA reached $1.0^{+4}$. This was followed by a 14-month break where this Chinese herb composition of the present invention was not taken. Instead, the patient took the same premade Chinese herb medicine and her VA reduced to 0.8, which equals a loss of 1 log line or a loss of ¼ of her 4-line visual gain. Fortunately, her VA improved to 1.0 again after the resumption of this Chinese herb composition of the present invention for eight weeks. In addition, her VA further improved to 1.2 after another eight weeks of the intake of the Chinese herb composition of the present invention.

Case 2: An Asian female in her 40s suffered from wet MMD for a decade, during which laser coagulation was done twice but her VA was the same. After twelve weeks of treatment with this Chinese herb composition of the present invention her VA increased from 0.4 to 1.0, which equals a gain of 4 log lines.

Case 3: An Asian male in his 70s suffered from wet AMD for years and received PDT treatment with no increase in VA in the better eye. After nine weeks of treatment with this Chinese herb composition of the present invention, the VA increased from 4.1 to 4.4 on a logarithmic vision chart, which is a 3-log line increase. During the same period of time, the VA of the other eye improved from FC/2m (finger count at 2 meter) to FC/3m.

Case 4: An Asian male in his 70s suffered from wet AMD in one eye for two years. After four intraocular injections of Avastin® during a 6-month period his VA increased from FC/2m to 4.0 (the first line on the logarithmic chart). After one month of treatment with the Chinese herb medicine of the present invention, his VA improved to 4.3, which is a gain of 3 log lines.

Unfortunately, embodiments of the present invention are not a cure of macular degeneration, just like the other drugs mentioned in the background section. As in Case 1, the patients experienced a loss of ¼ of the improved vision after a 16-month break. Therefore, intermittent maintenance of herb intake is necessary to keep the improved visual acuity.

The herbs used in this invention are also beneficial for general health. Most of the thirteen beneficiary effects listed above may apply to the brain, heart, liver, kidneys and so on. A noted effect in patients receiving the composition of the present invention, is that after taking this formula for some weeks, their blood pressure was slightly lowered, resulting in a reduction in the dosage of their regular blood pressure pills.

One point worth noting is that the ciliary body, a structure inside the eyeball, where the aqueous humor (clear liquid) is produced to maintain the intraocular pressure (TOP), may have improved function also as a response to the herb intake. As a result, an unwanted increase in TOP may occur if the patient has a problem in his or her aqueous humor draining system. Therefore, those patients who have a preexisting TOP problem, should have their TOP monitored during the herb treatment. However, no TOP problems have been encountered in the macular degeneration patients treated thus far.

The effect of the present invention could be further improved in two ways.

1. Adjusting the ingredients of the formula in the future, with updated knowledge regarding the disease and the pharmacology of Chinese herbs.

2. Combining the anti-VEGF agents with the present invention for a complementary effects. The anti-VEGF agents like Ranibizumab or Bevacizumab or VEGF-trap eye can inactivate the existing VEGF and eliminate some new blood vessels but with a narrow scope of action. The herbs in the present invention can help correct the underlying condition which initiates the production of the VEGF and have a wider scope of functions with a stronger potential of vision increase. And thus, a combined treatment may not only further advance the efficacy but also substantially reduce the frequency of the drug injection.

In summary, the present invention adapts traditional principles of TCM theory and modern understanding of both the disease and the herbs, utilizes a scientific way of herb selection, and creates comprehensive Chinese herb formulas that target most contributing factors and most pathologic changes for the treatment of macular degeneration. The clinical observations using the compositions of the present invention have demonstrated a superiority in efficacy and safety over other treatments.

The above detailed description of the Chinese herb composition for the treatment of macular degeneration and its preparation method according to embodiments of the present invention, is illustrative but not restrictive. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

I claim:

1. A Chinese herb composition for treating macular degeneration comprising: from about 0.8 to about 3.0 units by weight of *Salviae miltiorrhizae*, from about 0.3 to about 2.0 units by weight of *Chuanxiong rhizoma*, from about 0.6 to about 2.4 units by weight of *Lycii fructus*, from about 0.5 to about 2.0 units by weight of *Chrysanthemi flos*, from about 0.2 to about 1.2 units by weight of *Schisandrae chinensis fructus*, from about 0.9 to about 6.0 units by weight of *Imperatae rhizoma*, and from about 0.5 to about 2.0 units by weight of *Scutellariae radix*.

2. The Chinese herb composition according to claim 1, wherein the *Salviae miltiorrhizae* is 2.0 units by weight, the *Chuanxiong rhizoma* is 1.0 unit by weight, the *Lycii fructus* is 2.0 units by weight, the *Chrysanthemi flos* is 0.5 units by weight, the *Schisandrae chinensis fructus* is 1.0 unit by weight, the *Imperatae rhizoma* is 2.0 units by weight, and the *Scutellariae radix* is 1.0 unit by weight.

3. The Chinese herb composition according to claim 1, further comprising: *Rehmanniae radix praeparata*, *Angelicae sinensis radix*, *Astragali radix*, *Dendrobii caulis*, *Cassiae semen*, *Plantaginis semen*, *Alismatis rhizoma*, *Forsythiae fructus*, *Puerariae lobatae radix*, *Poria*, and *Dipsaci radix*.

4. The Chinese herb composition according to claim 3, comprising: *Salviae miltiorrhizae* from about 0.8 to about 3.0 units by weight, *Chuanxiong rhizoma* from about 0.3 to about 2.0 units by weight, *Lycii* fructus from about 0.6 to about 2.4 units by weight, *Chrysanthemi flos* from about 0.5 to about 2.0 units by weight, *Schisandrae chinensis fructus* from about 0.2 to about 1.2 units by weight, *Imperatae rhizoma* from about 0.9 to about 6.0 units by weight, *Scutellariae radix* from about 0.5 to about 2.0 units by weight, *Rehmanniae radix praeparata* from about 0.7 to about 3.0 units by weight, *Angelicae sinensis radix* from about 0.4 to about 2.4 units by weight, *Astragali radix* from about 0.6 to about 6.0 units by weight, *Dendrobii caulis* from about 0.6 to about 2.4 units by weight, *Cassiae semen* from about 0.9 to about 3.0 units by weight, *Plantaginis semen* from about 0.6 to about 3.0 units by weight, *Alismatis rhizoma* from about 0.4 to about 1.8 units by weight, *Forsythiae fructus* from about 0.4 to about 3.0 units by weight, *Puerariae lobatae radix* from about 0.8 to about 3.0 units by weight, *Poria* from about 0.5 to about 3.0 units by weight, and *Dipsaci radix* from about 0.7 to about 3.0 units by weight, respectively.

5. The Chinese herb composition according to claim 3, wherein the *Salviae miltiorrhizae* is 2.0 units by weight, the *Chuanxiong rhizoma* is 1.0 unit by weight, the *Lycii fructus* is 2.0 units by weight, the *Chrysanthemi flos* is 1.0 unit by weight, the *Schisandrae chinensis fructus* is 1.0 unit by weight, the *Imperatae rhizoma* is 2.0 units by weight, the *Scutellariae radix* is 1.0 unit by weight, the *Rehmanniae radix praeparata* is 2.0 units by weight, the *Angelicae sinensis radix* is 1.0 unit by weight, the *Astragali radix* is 2.0 units by weight, the *Dendrobii caulis* is 2.0 units by weight, *Cassiae semen* is 2.0 units by weight, the *Plantaginis semen* is 2.0 units by weight, the *Alismatis rhizoma* is 1.3 units by weight, the *Forsythiae fructus* is 1.3 units by weight, the *Puerariae lobatae radix* is 2.0 units by weight, the *Poria* is 2.0 units by weight, and the *Dipsaci radix* is 2.0 units by weight.

6. The Chinese herb composition according to claim 3, further comprising *Silybi fructus* or *Silybin*.

7. The Chinese herb composition according to claim 4, further comprising *Silybi* fructus from about 0.5 to about 3.0 units by weight.

8. The Chinese herb composition according to claim 4, further comprising *Silybin* from about 0.035 to about 0.14 units by weight.

9. The Chinese herb composition according to claim 5, further comprising 0.5 units by weight of *Silybi fructus*.

10. The Chinese herb composition according to claim 5, further comprising 0.035 units by weight of *Silybin*.

11. The Chinese herb composition according to claim 1, wherein said composition is administered orally.

12. The Chinese herb composition according to claim 1, wherein said composition is in a form selected from the group consisting of a capsule, a tablet, a pill, a granulate, a pellet, a solid mixture, a dispersion in liquid phases, a suspension, an emulsion, a powder, a solution and a paste.

13. The Chinese herb composition according to claim 12, wherein said composition is in a form selected from the group consisting of a suspension, an emulsion, a solution and a paste; and is administered parenterally.

14. A method for preparing the Chinese herb composition for treating macular degeneration of claim 1, comprising the steps of:
    obtaining a five-fold concentrated herb extract powder of each herbal component;
    mixing evenly each of said concentrated herb extract powder according to said number of units by weight to form a mixed herb extract powder composition; and placing said mixed herb extract powder composition into a form selected from the group consisting of tablets, pills, granulates, pellets, capsules, paper bags and plastic bags, solid mixtures, dispersions in liquid phases, suspensions, emulsions, solutions and pastes.

15. The method of claim 14, wherein each of said capsules is a No. 0 sized capsule, wherein each of said capsules contains about 0.5 g of the mixed herb extract powder composition.

16. The method of claim 14, wherein said paper bags are non-toxic medical paper bags, where each of said paper bags contains about 5.0 g of the mixed herb extract powder composition.

17. The method of claim 14, wherein said plastic bags are opaque, non-toxic medical plastic bags, wherein each of said plastic bags contains about 5.0 g of the mixed herb extract powder composition.

* * * * *